US012636716B2

(12) United States Patent
Morales et al.

(10) Patent No.: US 12,636,716 B2
(45) Date of Patent: May 26, 2026

(54) MEDICAL INSTRUMENT AND METHOD FOR PRODUCING A MEDICAL INSTRUMENT

(71) Applicant: Aesculap AG, Tuttlingen (DE)

(72) Inventors: Daniel Morales, Nendingen (DE);
Dominic Faitsch, Neuhausen (DE);
Daniel Weisser,
Villingen-Schwenningen (DE)

(73) Assignee: Aesculap AG, Tuttlingen (DE)

( * ) Notice: Subject to any disclaimer, the term of this
patent is extended or adjusted under 35
U.S.C. 154(b) by 313 days.

(21) Appl. No.: 18/125,904

(22) Filed: Mar. 24, 2023

(65) Prior Publication Data

US 2023/0225751 A1 Jul. 20, 2023

Related U.S. Application Data

(63) Continuation of application No.
PCT/EP2021/076290, filed on Sep. 24, 2021.

(30) Foreign Application Priority Data

Sep. 25, 2020 (DE) ..................... 10 2020 125 070.3

(51) Int. Cl.
*B23C 3/00* (2006.01)
*B23C 3/30* (2006.01)
(Continued)

(52) U.S. Cl.
CPC .................. *B23C 3/00* (2013.01); *B23C 3/30*
(2013.01); *A61B 2017/00526* (2013.01);
(Continued)

(58) Field of Classification Search
CPC . A61B 17/30–2017/308; A61B 17/282; A61B
2017/00526; A61B 17/28–295;
(Continued)

(56) References Cited

U.S. PATENT DOCUMENTS 2,668,538 A * 2/1954 Baker .................. A61B 17/282
81/426
3,815,607 A * 6/1974 Chester .................. A61B 17/30
294/99.2
(Continued)

FOREIGN PATENT DOCUMENTS

DE 2346400 A1 3/1974

OTHER PUBLICATIONS

Article "What is CNC Milling? Everything You Need to Know
About CNC Milling", by Star Rapid, Jul. 16, 2019, 13 pages, from
https://www.starrapid.com/blog/everything-you-need-to-know-about-
cnc-milling/.*
(Continued)

*Primary Examiner* — Erica E Cadugan
(74) *Attorney, Agent, or Firm* — Christopher A. Rothe;
CM Law

(57) ABSTRACT

A medical instrument and method for producing a medical
instrument. The medical instrument includes at least one
instrument arm. A toothing with at least two teeth is formed
on a distal end of the instrument arm. Each of the teeth
project transversely from the distal end and has two tooth
flanks facing away from one another. Each tooth flank has at
least one planar first surface region and at least one planar
second surface region. The at least one planar first surface
region and the at least one planar second surface region are
inclined toward one another by a surface region angle. The
first and second surface regions are formed by milling, in
particular with a CNC machine.

8 Claims, 10 Drawing Sheets

(51) Int. Cl.

| | |
|---|---|
| *A61B 17/00* | (2006.01) |
| *A61B 17/28* | (2006.01) |
| *A61B 17/30* | (2006.01) |

(52) U.S. Cl.
CPC ............. *A61B 17/282* (2013.01); *A61B 17/30* (2013.01); *B23C 2220/00* (2013.01); *Y10T 409/303752* (2015.01)

(58) Field of Classification Search
CPC .......................... A61B 17/50–2017/505; Y10T 409/30–409/309968; Y10S 294/902
USPC ........ 294/99.2, 902; 606/210–211, 205–209; 409/64–242
See application file for complete search history.

(56) References Cited

U.S. PATENT DOCUMENTS

| | | | |
|---|---|---|---|
| 3,815,609 A | | 6/1974 | Chester |
| 3,879,813 A | * | 4/1975 | Shadwell ............. A61B 17/282 24/459 |
| 5,613,499 A | | 3/1997 | Palmer et al. |
| 2005/0065538 A1 | | 3/2005 | Van Wyk |
| 2016/0151083 A1 | | 6/2016 | Mottola et al. |
| 2021/0381071 A1 | * | 12/2021 | Barthelmes ........ A61B 17/2812 |

OTHER PUBLICATIONS

Search Report received in International Application No. PCT/EP2021/076290, dated Dec. 21, 2021, with translation, 4 pages.

\* cited by examiner

MEDICAL INSTRUMENT AND METHOD FOR PRODUCING A MEDICAL INSTRUMENT

CROSS-REFERENCE TO RELATED APPLICATIONS

This application is a continuation of International Application No. PCT/EP2021/076290 filed Sep. 24, 2021 and claims priority to German Application No. 10 2020 125 070.3 filed Sep. 25, 2020. The contents of International Application No. PCT/EP2021/076290 and German Application No. 10 2020 125 070.3 are incorporated herein by reference in their entireties and for all purposes.

FIELD

The present invention relates to medical instruments generally, and more specifically to a medical instrument having at least one instrument arm, wherein formed on a distal end of the instrument arm is a toothing with at least two teeth, which project transversely from the distal end, wherein each of the at least two teeth have two tooth flanks facing away from one another.

Furthermore, the present invention relates to methods for producing a medical instrument generally, and more specifically to a method for producing a medical instrument, which comprises at least one instrument arm, wherein formed on a distal end of the instrument arm is a toothing with at least two teeth, which project transversely from the distal end, wherein each of the at least two teeth have two tooth flanks facing away from one another.

BACKGROUND

Medical instruments of the kind described at the outset are known, in particular, in the form of tweezers with toothings on distal ends of tweezer arms of the tweezers, wherein the toothings comprise one or more so-called mouse teeth, which interengage in a closing position of the tweezers. The production of instruments of that kind entails considerable time and effort. The toothings are typically made by hand and require a surgery technician with a high level of skill so that the toothings perfectly interengage in the closing position.

SUMMARY

In a first aspect of the invention, a medical instrument has at least one instrument arm. Formed on a distal end of the instrument arm is a toothing with at least two teeth, which project transversely from the distal end. Each of the at least two teeth has two tooth flanks facing away from one another. Each tooth flank has at least one planar first surface region and at least one planar second surface region. The at least one planar first surface region and the at least one planar second surface region are inclined toward one another by a surface region angle. The first and second surface regions are formed by milling, in particular with a CNC machine.

In a second aspect of the invention, a method for producing a medical instrument is provided. Said medical instrument comprises at least one instrument arm. Formed on a distal end of the instrument arm is a toothing with at least two teeth, which project transversely from the distal end. Rach of the at least two teeth have tooth flanks facing away from one another. Each tooth flank is configured having at least one planar first surface region and at least one planar second surface region. The at least one planar first surface region and the at least one planar second surface region are inclined toward one another by a surface region angle. The first and second surface regions are formed by milling, in particular with a CNC machine.

BRIEF DESCRIPTION OF THE DRAWING FIGURES

The foregoing summary and the following description may be better understood in conjunction with the drawing figures, of which:

DETAILED DESCRIPTION

Although the invention is illustrated and described herein with reference to specific embodiments, the invention is not intended to be limited to the details shown. Rather, various modifications may be made in the details within the scope and range of equivalents and without departing from the invention.

Figure 10:
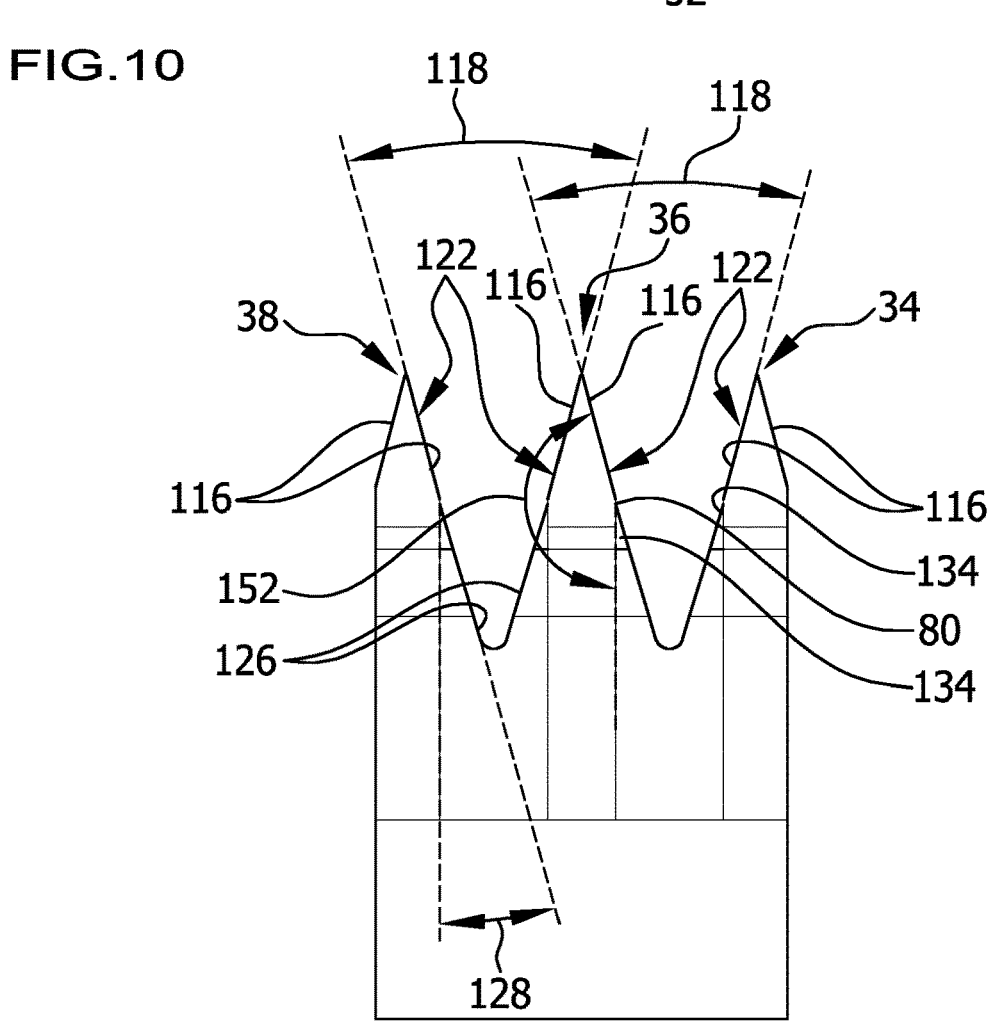
FIG. 10 shows a view of the arrangement from FIG. 9 in the direction of arrow C.
Figure 11:
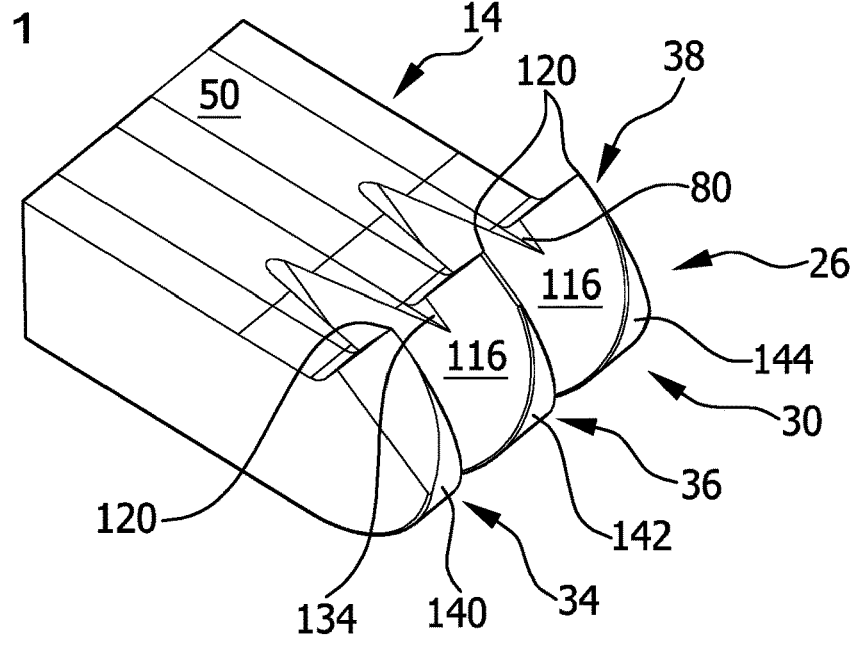
FIG. 11 shows a perspective view of the distal end region of the instrument arm after a further machining step.
Figure 12:
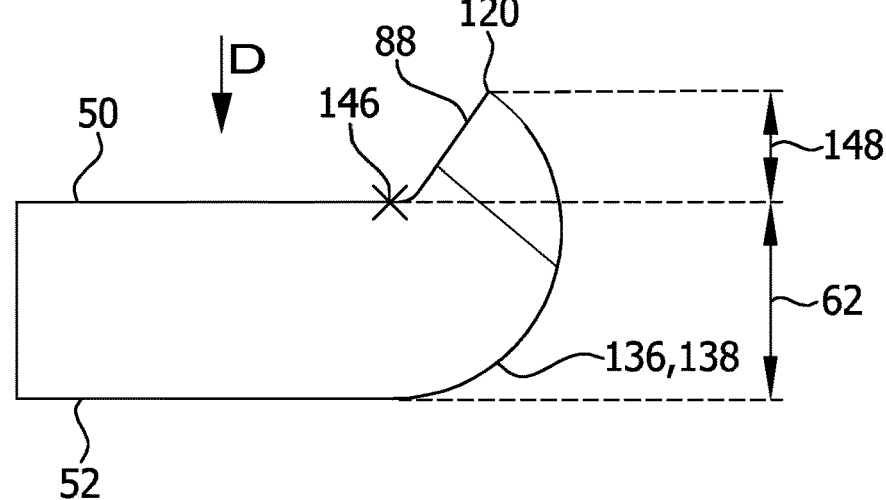
FIG. 12 shows a side view of the arrangement from FIG. 11.
Figure 13:
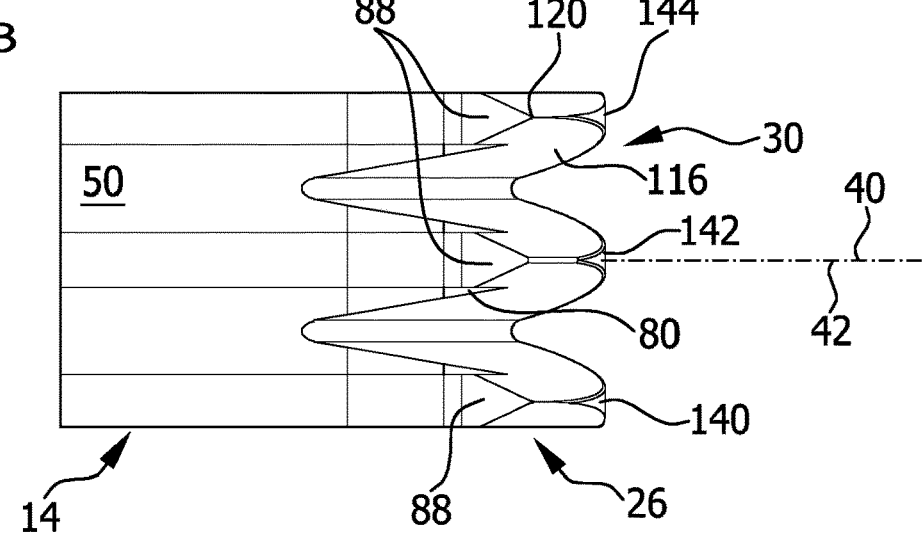
FIG. 13 shows a view of the arrangement from FIG. 12 in the direction of the arrow D.

The present invention relates to a medical instrument having at least one instrument arm, wherein formed on a distal end of the instrument arm is a toothing with at least two teeth, which project transversely from the distal end, wherein each of the at least two teeth has two tooth flanks facing away from one another, wherein each tooth flank has at least one planar first surface region and at least one planar second surface region, wherein the at least one planar first surface region and the at least one planar second surface region are inclined toward one another by a surface region angle (see, e.g., surface region angle 152 in FIG. 10), and wherein the first and second surface regions are formed by milling, in particular with a CNC (numerically-controlled) machine.

The proposed configuration of the toothing of the at least one instrument arm makes it possible, in particular, to form the teeth in a simple manner, in particular fully automatically, for example with a CNC machine. Merely milling tools are required for forming the first and second surface regions. In particular, the surface regions inclined toward one another can be formed with two different milling tools. For example, rotational axes of the milling tools can be inclined toward one another during production. Furthermore, the surface regions on each tooth flank inclined toward one another make it possible that, if the instrument comprises two instrument arms with toothings that interengage in a closing position, the toothings do not have to be reworked or have to be reworded only minimally by hand for them to completely and perfectly interengage. In particular, by forming the first surface region, it is possible to abut the instrument arms completely against one another in the closing position of the instrument. Due to the particular design of the toothing, it is possible, in particular, to form them completely by machine. A production time can thus be shortened and costs associated with production can be reduced. There is also no particular manual skill required to form the toothing.

It is favorable if the two tooth flanks of each of the at least two teeth are of mirror-symmetrical or substantially mirror-symmetrical configuration relative to a tooth mirror plane and if an intersection line (see, e.g., intersection line 150 in FIG. 5) of the at least two second surface regions of the respective tooth lies in the tooth mirror plane. Teeth configured in that way enable an optimal closing of the instrument in the closing portion, i.e., when toothings of two instruments arms interengage.

The toothing can be formed in a simple manner and with a high symmetry if a tooth tip of the tooth lies on the intersection line of the at least two second surface regions of the respective tooth.

It is favorable if a distal end region of the at least one instrument arm defines a longitudinal direction and if the toothing is configured projecting transversely relative to the longitudinal direction. Tweezers, for example, can thus be formed in a simple manner with two such instrument arms.

It is advantageous if the instrument arm, in particular its distal end region, has a planar top side and if the toothing projects at least partially beyond the top side. Instruments with instrument arms of that kind can be used, in particular, to prepare tissue in a precise and delicate manner.

It is favorable if each first surface region defines with the top side a first top side intersection line and if each second surface region defines with the top side a second top side intersection line. This configuration enables, in particular, an optimal interengagement of cooperating toothings that are formed on two instrument arms.

In order to enable, in particular, a good interengagement of toothings on two instrument arms, it is advantageous if the first top side intersection line and the second top side intersection line of the same tooth flank enclose an acute angle opening in the proximal direction.

The toothing can be formed using a conical milling cutter in a simple manner if the second top side intersection lines of adjacent teeth of the toothing define an acute angle opened pointing in the distal direction.

It is advantageous if the first surface region and the second surface region of a tooth flank and the top side come into contact at a point of intersection of the first top side intersection line and the second top side intersection line. A perfect interengagement of toothings that are formed on two cooperating instrument arms can be achieved in this way.

The first top side intersection line preferably extends in parallel or substantially in parallel to the longitudinal direction. This has the advantage, in particular, that toothings on two cooperating instrument arms are able to optimally interengage.

It is favorable if each first surface region together with a sloped face, which is inclined relative to the top side by a slope angle, defines a first sloped face intersection line, and if each second surface region together with the sloped face defines a second sloped face intersection line. It is thus possible, in particular, to have toothings on distal ends of cooperating instrument arms completely interengage even when the longitudinal axes of the instrument arms are aligned not in parallel to one another, but instead extend toward one another in the distal direction, i.e. enclose with one another an opening angle in the proximal direction. This may be the case, in particular, when the instrument arms are of elastic configuration and are configured somewhat bulged pointing away from one another. If no parallel orientation of the instrument arms in the region of their distal ends can be ensured, the sloped face inclined relative to the top side by the slope angle then enables, as described, an improved cooperation of the toothings of the two instrument arms. The design of the sloped face corresponds substantially to the surface region described above, which is delimited by the first top side intersection line and the second top side intersection line. However, this surface region extends in parallel to the top side. The sloped face is inclined relative to the top side as specified.

It is advantageous if the slope angle has a value in a range of about 3° to about 30°. In particular, the slope angle may have a value in a range of about 8° to about 13°. Further in particular, a value of the slope angle may be about 10°. Providing the slope angle in the specified ranges has the advantage, in particular, that toothings on distal ends of instrument arms that do not extend in parallel are also able to optimally interengage.

It is favorable if the sloped face and the top side intersect in a sloped face top side intersection line, which extends transversely, in particular perpendicularly, to the longitudinal direction. The sloped face top side intersection line thus forms a boundary line of the sloped face in the proximal direction.

It is advantageous if the first sloped face intersection line and the second sloped face intersection line of the same tooth flank enclose an acute angle opening in the proximal direction. This design enables, in particular, a good interengagement of toothings on two instrument arms.

The toothing can be formed using a conical milling cutter in a simple manner if the second sloped face intersection lines of adjacent teeth of the toothing define an acute angle opened pointing in the distal direction.

It is favorable if the first surface region and the second surface region of a tooth flank and the sloped face come into contact at a point of intersection of the first sloped face intersection line and the second sloped face intersection line. In particular, an improved interengagement of toothings that are formed on two cooperating instrument arms can thus be achieved.

The first sloped face intersection line and the longitudinal direction are preferably inclined toward one another by the sloped angle. Thus, in particular, toothings on two cooperating instrument arms are better able to interengage when the instrument arms are not aligned in parallel to one another, but instead enclose an opening angle pointing in the proximal direction.

The at least two first surface regions of the two tooth flanks facing away from one another favorably extend in parallel or substantially in parallel to one another. This makes it possible, in particular, to bring a corresponding toothing into engagement with the toothing in a closing position of the instrument, namely in such a way that top sides of the instrument arms, projecting from which are the toothings, abut against one another in a closing position.

The toothing can be formed in a simple manner if the at least one first surface region is formed using a first milling tool. In particular, it may be made using a cylindrical milling cutter, which is also referred to as an end milling cutter. The first surface regions can thus be formed in parallel to one another and perpendicular to the top side of the instrument arm in a simple manner. Instead of a cylindrical milling cutter, saw blades may also be used, with which the at least one first surface region is formed by sawing.

In order to minimize a number of working steps, it is advantageous if a surface spacing of the first surface regions of adjacent teeth corresponds to a diameter of the cylindrical milling cutter.

A machine production of the toothing can be achieved in a simple manner, in particular, by the at least one planar second surface region being formed using a second milling tool, in particular a first conical milling cutter. In particular, the at least one planar second surface region of the tooth flank can be formed after the formation of the first surface regions of the toothing.

Furthermore, provision may be made that each tooth has at least one planar third surface region. The latter may be configured facing in the proximal direction and inclined relative to the top side.

The production of the instrument can be realized in a simple manner, in particular, if the at least one third surface region is made by cold forming or by milling, in particular with a CNC machine. Machining the toothing by milling is necessary, in particular, only when the third surface region cannot be formed in the desired manner by cold forming. An uneven surface made by cold forming can be made planar in a simple manner through the milling.

The formation of the at least one third surface region can be realized in a simple manner if it is made using a third milling tool. In particular, the third milling tool may be configured in the form of a second conical milling cutter. Thus, a tooth flank with a first and a second surface region as well as a third surface region of a tooth can be formed by machine in the described manner with only three milling operations.

It is advantageous if the at least one third surface region has common intersection lines with the at least two first surface regions and with the at least two second surface regions of the respective tooth. In particular, a completely symmetrical tooth can be formed in this way.

In order to be able to prepare tissue securely and delicately, it is favorable if the at least one third surface region together with the top side encloses an opening angle and if the opening angle has a value of at least 90°.

The opening angle preferably has a value in a range of about 110° to about 140°. In particular, it may have a value of about 125°. With teeth of that kind, tissue can be gripped and handled in a secure manner.

The opening angle can be easily configured having a desired angle if it corresponds to half of a cone angle of the second conical milling cutter plus 90°. The at least one third surface region can then be formed in a simple manner by a conical milling cutter being moved transversely to the longitudinal direction past the teeth, a longitudinal axis of the conical milling cutter extending perpendicularly to the top side.

Furthermore, it is advantageous if the third surface region defines a third surface region plane, if the third surface region plane and the top side define a third top side intersection line, and if the third top side intersection line extends transversely, in particular perpendicularly, to the longitudinal direction. In particular, hook-shaped teeth can thus be formed in a simple manner.

The instrument can be formed in a simple manner if the at least one instrument arm is made from an instrument arm blank. Thus, in particular, an instrument arm blank can be provided, which comprises a projection on the distal end that is machined as described to form the toothing on the instrument arm, in particular by machine milling.

It is favorable if the instrument arm blank has an arm portion with a rectangular cross section, which extends in the distal direction, and if a tooth projection projecting transversely, in particular perpendicularly, is formed on a distal arm portion end, and if the toothing is formed on the tooth projection. The tooth projection may have, in particular, a form or outer contour that can be altered, for example exclusively by machining, in order to form the toothing. The tooth projection is, in particular, preferably only so large that only a minimal amount of material has to be removed from an outer contour of said tooth projection in order to produce the toothing.

It is advantageous if the instrument blank is made of a metallic material by cold forming. In particular, it may be made of an instrument steel. Such an instrument blank can be provided in a simple and cost-effective manner.

The toothing preferably comprises at most six teeth. This makes it possible, in particular, to provide instruments with a sufficient number of teeth, but to limit a width of the instrument to a reasonable level.

The second surface regions of adjacent teeth favorably define between them a wedge angle. This design makes it possible, in particular, to form the two surface regions of adjacent teeth with a conical milling cutter.

In order to be able to ensure a function of the toothing in the desired manner, it is advantageous, in particular, if the wedge angle has a value in a range of about 15° to about 45°. In particular, it may have a value of about 25° to about 35°. In particular, such wedge angles can be produced with conical milling cutters in a simple manner.

The handling and the production of the instrument are significantly simplified if the toothing is configured mirror-symmetrically to a toothing mirror plane extending in the longitudinal direction. In particular, this simplifies a programming of a CNC machine for forming the toothing.

In accordance with a further preferred embodiment of the invention, provision may be made that each second surface region defines a second surface region plane, that the second surface region planes of adjacent teeth define a common surface region intersection line, and that the surface region intersection line together with the longitudinal direction encloses an angle of inclination opened in the distal direction. Such a design can be achieved in a simple manner with a conical milling cutter, the longitudinal axis of which is moved perpendicularly to the surface region intersection line.

In order to enable a good closing result upon the interengagement of two toothings of two instrument arms, it is advantageous if the angle of inclination has a value in a range of about 30° to about 50°. In particular, the angle of inclination may be about 40°.

It is favorable if each tooth flank has a notch in the second surface region and if the notch is delimited by the first surface region on the one hand and by the top side on the other hand. Such a notch ensures, in particular, that two correspondingly formed toothings in which the tooth flanks have notches of that kind are able to optimally interengage. In particular, it is thus possible for top sides of the instrument arms to be able to abut against one another in a closing position.

An end face of the toothing that faces in the distal direction is preferably rounded. The instrument can thus be inserted into tissue without damaging it.

In order to be able to form as atraumatic an instrument as possible, it is favorable if the end face extends from a bottom side of the instrument arm, which faces in a direction opposite to the top side, up to the tooth tip. This makes it possible, in particular, to form a distal end of the instrument with two instrument arms such that practically no sharp edges remain when the toothings of the two instrument arms interengage with one another.

The end face can be rounded off in a simple manner if it defines a cylindrical surface and if a cylinder longitudinal axis of the cylindrical surface extends transversely, in particular perpendicularly, to the longitudinal direction and in parallel to the top side. The end face may thus, in particular, have the form of a half cylinder. Cooperating toothings with correspondingly formed end faces may then define a half-cylindrically shaped distal end of the instrument in the closing position.

The risk of damage to tissue by the medical instrument can be minimized in a simple manner, in particular, by the end face defining a section of a spherical surface or being of substantially spherical configuration.

In order to achieve sufficient stability of the instrument, in particular in the region of the toothing, it is advantageous if a distance of the tooth tip from the top side is smaller than a thickness of the instrument arm in the region of its distal end and if the thickness is defined by a distance of the top side from the bottom side. In other words, the tooth tip projects from the top side no further than the instrument arm in the region of the distal end is thick.

In accordance with a further preferred embodiment of the invention, provision may be made that the instrument comprises two instrument arms, that formed on a first instrument arm of the two instrument arms is a first toothing, which points in the direction toward a second instrument arm of the two instrument arms, that formed on the second instrument arm is a second toothing, which points in the direction toward the first instrument arm, and that in a closing position of the instrument in which distal ends of the two instrument arms are maximally proximate to one another, the first toothing and the second toothing interengage. Such an instrument may be configured, e.g., in the form of tweezers, with which tissue can be handled in a simple and secure manner. In particular, the two instrument arms of the instrument may be formed separately from one another. For example, the instrument arms may be connected to one another at proximal ends.

The second toothing preferably comprises one more tooth than the first toothing. The instrument arms can thus extend completely in parallel to one another. If, for example, one toothing has two teeth and the other three teeth, the two teeth can engage into the recesses between the three teeth in the closing position. In particular, both toothings may be formed mirror-symmetrically to a common mirror plane of the instrument. Thus, in particular, a nearly perfectly closed distal end of the instrument can be formed in a closing position.

The configuration of the instrument can be further simplified, in particular, by the teeth of the first toothing and the second toothing being identically or substantially identically shaped.

In, particular, in order to be able to handle tissue in a simple and secure manner, it is advantageous if the instrument is configured in the form of tweezers.

Further, the invention relates to a method for producing a medical instrument, which comprises at least one instrument arm, wherein formed on a distal end of the instrument arm is a toothing with at least two teeth, which project transversely from the distal end, wherein each of the at least two teeth have tooth flanks facing away from one another, wherein each tooth flank is configured having at least one planar first surface region and at least one planar second surface region, wherein the at least one planar first surface region and the at least one planar second surface region are inclined toward one another by a surface region angle, and wherein the first and second surface regions are formed by milling, in particular with a CNC machine.

As already explained above, with this method, a medical instrument, in particular a toothing thereof, can be formed completely or substantially completely by machine. Instruments of that kind can thus be made significantly faster than instruments made conventionally by hand. This is also more cost-effective and enables a higher reproducibility of instruments with consistent quality.

It is favorable if the two tooth flanks of each of the at least two teeth are configured mirror-symmetrically or substantially mirror-symmetrically relative to a tooth mirror plane and if an intersection line of the at least two second surface regions of the respective tooth lies in the tooth mirror plane. If two toothings are configured having teeth of that kind, it can be ensured, in particular, in a simple manner that the toothings are able to optimally interengage with one another in a closing position.

Production of the instrument becomes particularly simple if a tooth tip of the tooth is formed, which lies on the intersection line of the at least two second surface regions of the respective tooth. Furthermore, in particular, an interengagement of corresponding toothings that are formed on two instruments arms can thus be improved.

It is favorable if a distal end region of the at least one instrument arm defines a longitudinal direction and if the toothing is configured projecting transversely relative to the longitudinal direction. With a toothing oriented in that way, in particular, tissue can be optimally gripped and manipulated.

It is advantageous if the instrument arm, in particular the distal end region thereof, has a planar top side and if the toothing is configured projecting at least partially beyond the top side. The toothing can thus be used like a hook for handling tissue, in particular for preparing it.

It is favorable if each first surface region is configured in such a way that together with the top side it defines a first top side intersection line and if each second surface region is configured in such a way that together with the top side it defines a second top side intersection line. In particular, first and second surface regions inclined toward one another can thus be achieved in a simple manner for forming a tooth flank of the tooth. In particular, an interengagement of corresponding toothings can also be improved with surface regions formed in that way.

Preferably each tooth flank is configured in such a way that the first top side intersection line and the second top side intersection line enclose an acute angle opening in the proximal direction. In particular, a notch or set-back portion can thus be formed on each tooth flank, which is delimited partially by a first surface region and partially by the top side of the instrument arm in the region of its distal end.

Toothings formed corresponding to one another can be configured to be able to engage in one another in a simple manner if the toothing is configured in such a way that the second top side intersection lines of adjacent teeth define an acute angle opened pointing in the distal direction. In particular, this angle can result from a conical milling tool, which is used to form the second surface regions.

It is favorable if the toothing is configured in such a way that the first surface region and the second surface region of a tooth flank and the top side come into contact at a point of intersection of the first top side intersection line and the second top side intersection line. At the point of intersection, the first and second surface regions thus not only adjoin one another, but also the top side.

The teeth are preferably configured in such a way that the first top side intersection line extends in parallel or substantially in parallel to the longitudinal direction. This makes it possible, in particular, to have corresponding toothings engage in one another in parallel to the longitudinal direction.

It is favorable if each first surface region is configured in such a way that together with a sloped face, which is inclined relative to the top side by a slope angle, it defines a first sloped face intersection line, and if each second surface region is configured in such a way that together with the sloped face it defines a second sloped face intersection line. In particular, first and second surface regions inclined toward one another can thus be achieved in a simple manner for forming a tooth flank of the tooth. Also, in particular, an interengagement of corresponding toothings with surface regions formed in that way can be improved, since the sloped faces inclined relative to the top side make it possible for toothings of cooperating distal ends of two instrument arms of a medical instrument to be able to interengage even when the instrument arms in the region of their distal ends extend not in parallel to one another, but instead extend toward one another in the distal direction and thus define an opening angle pointing in the proximal direction.

It is advantageous if the slope angle is configured having a value in a range of about 3° to about 30°. In particular, the slope angle may be configured having a value in a range of about 8° to about 13°. Further in particular, the slope angle may have a value of about 10°. Providing a slope angle in the stated ranges makes it possible, in particular, to incline distal ends of two cooperating instrument arms toward one another by twice the slope angle, a good interengagement of the toothings formed on the distal ends of the instrument arms then still being made possible.

It is favorable if each first surface region is configured in such a way that the sloped face and the top side intersect in a sloped face top side intersection line, which extends transversely, in particular perpendicularly, to the longitudinal direction. The sloped face top side intersection line thus delimits the sloped face in the proximal direction.

It is advantageous if each tooth flank is configured in such a way that the first sloped face intersection line and the second sloped face intersection line of the same tooth flank enclose an acute angle opening in the proximal direction. This makes it possible, in particular, to form on each tooth flank a notch or set-back portion, which is delimited partially by a first surface region and partially by the sloped face in the region of its distal end.

It is favorable if the toothing is configured in such a way that the second sloped face intersection lines of adjacent teeth of the toothing define an acute angle opened pointing in the distal direction. In particular, toothings that are formed corresponding to one another can thus be configured to be able to engage in one another in a simple manner. In particular, the defined acute angle can result from a conical milling cutter, which is used to form the second surface regions.

It is advantageous if the toothing is configured in such a way that the first surface region and the second surface region of a tooth flank and the sloped face come into contact at a point of intersection of the first sloped face intersection line and the second sloped face intersection line. At the point of intersection, the first and second surface regions thus not only adjoin one another, but also the sloped face.

In order to enable an optimal interengagement of toothings of cooperating instrument arms, it is advantageous if teeth are configured in such a way that the first sloped face intersection line and the longitudinal direction are inclined toward one another by the sloped angle.

In accordance with a further preferred embodiment of the invention, provision may be made that the teeth are configured in such a way that the at least two first surface regions of the two tooth flanks facing away from one another extend in parallel or substantially in parallel to one another. This makes it possible, in particular, in the case of corresponding toothings, for the first surface regions of the one toothing and the first surface regions of the other toothing to be aligned in parallel to one another when the toothings interengage with one another. An interengagement of the toothings can thus be improved.

It is favorable if the at least one first surface region is made with a first milling tool. In particular, the first milling tool may be configured in the form of a cylindrical milling cutter. Here, it is favorable if a longitudinal axis of the cylindrical milling cutter during milling is oriented both perpendicularly to the top side and perpendicularly to the longitudinal direction. Thus, in a first step, a tooth base extending in the distal direction can be formed on a tooth projection on an instrument arm blank using the cylindrical milling cutter. Instead of the cylindrical milling cutter, a saw blade may also be used to form the at least one first surface region. In order to be able to alternatively form, in particular, a sloped face, it is favorable if, during milling, a longitudinal axis of the cylindrical milling cutter together with the longitudinal direction defines a milling plane, which extends perpendicularly to the top side and is inclined in the distal direction by a milling cutter longitudinal axis angle. In particular, the milling cutter longitudinal axis angle corresponds to the slope angle. Thus, a sloped face can be formed in a simple manner with a cylindrical milling cutter, the longitudinal axis of which does not extend in parallel to the top side of the instrument arm.

In order to minimize a number of milling operations, it is advantageous if the toothing is configured in such a way that a surface spacing of the first surface regions of adjacent teeth corresponds to a diameter of the cylindrical milling cutter In accordance with a further preferred embodiment of the invention, provision may be made that the at least one planar second surface region is made using a second milling tool. In particular, the second milling tool may be configured in the form of a first conical milling cutter. Furthermore, it may be advantageous if, during milling, a longitudinal axis of the first conical milling cutter is inclined relative to the top side by an angle of inclination opened in the distal direction and together with the longitudinal direction defines a plane extending perpendicularly to the top side. The longitudinal axis of the first conical milling cutter is thus moved in the described plane, and not in the longitudinal direction but instead obliquely relative thereto. The second surface regions of adjacent teeth can thus be formed, for example, in one single machining step.

Each tooth is favorably configured having at least one planar third surface region. The third surface region may define, in particular, a retaining face for retaining tissue. The third surface region may be configured, in particular, facing at least partially in the proximal direction.

The third surface region can be formed in a simple manner if it is made by cold forming or by milling. In particular, it may be machine made by milling using a CNC machine. A formation of the third surface region by cold forming can be realized by providing an instrument arm blank that already has the third surface region and is made by cold forming.

It is favorable if the at least one third surface region is made using a third milling tool. In particular, it may be a second conical milling cutter. In particular, a longitudinal axis of the second conical milling cutter during milling may be oriented both perpendicularly to the top side and perpendicularly to the longitudinal direction. A second conical milling cutter oriented in that way can be moved, in particular, transversely to the longitudinal direction in order to form the at least one third surface region on all teeth of the toothing.

It is advantageous if the tooth is configured in such a way that the at least one third surface region has common intersection lines with the at least two first surface regions and with the at least two second surface regions of the respective tooth. Thus, in particular, by forming the first surface regions, a set-back portion or notch that is delimited by the top side of the instrument arm and the first surface region can be formed on each tooth or on each tooth flank.

It is favorable if the at least one third surface region together with the top side encloses an opening angle and if the opening angle has a value of at least 90°. The opening angle is preferably an obtuse angle. This makes it possible, in particular, for tissue to be able to slide from the at least one third surface region of the tooth in the distal direction when the instrument arm is moved with the toothing in the proximal direction.

The opening angle is preferably configured having a value in a range of about 110° to about 140°. In particular, the opening angle may have a value of about 125°. Such opening angles can be formed in a simple manner, in particular, using conical milling cutters with corresponding cone angles.

The toothing can be realized in a simple manner if the opening angle is given by half of a cone angle of the second conical milling cutter plus 90°.

Furthermore, it may be advantageous if the tooth is configured in such a way that the third surface region defines a third surface region plane, that the third surface region plane and the top side define a third top side intersection line, and that the third top side intersection line extends transversely, in particular perpendicularly, to the longitudinal direction. Such a tooth can be formed in a simple manner by a conical milling cutter with its longitudinal axis perpendicular to the top side being moved in a direction perpendicular to the longitudinal direction. Thus, in particular, all third surface regions of the toothing can be formed in one operation.

The production of the instrument can be further simplified, in particular, if the at least one instrument arm is made from an instrument arm blank. For example, the instrument arm blank can be made by cold forming. In particular, it may be provided as a semi-finished product for the production of the instrument.

It is favorable if the instrument arm blank is configured having an arm portion extending in the distal direction with a rectangular cross section and having a tooth projection projecting transversely, in particular perpendicularly, on a distal arm portion end, and if the toothing is formed on the tooth projection. In particular, the tooth projection may be used as a raw form for part of the toothing. The toothing may thus be formed, in particular, exclusively by machining the instrument arm blank.

An instrument arm blank can be formed in a favorable manner if it is made of a metallic material by cold forming. For example, the metallic material may be an instrument steel. Sufficient stability of the instrument can thus be achieved.

The toothing is preferably configured having at most six teeth. For example, the toothing may also have three, four, or five teeth. Such toothings can be easily produced. In addition, a width of a distal end of the instrument can thus be minimized to a handleable size.

It is favorable if the toothing is configured in such a way that the second surface regions of adjacent teeth define between them a wedge angle. Such a toothing can be formed in a simple manner, in particular, by a conical milling cutter being used to machine the instrument arm blank for forming the second surface regions.

It is advantageous if the wedge angle is predetermined by the first conical milling cutter and has a value in a range of about 15° to about 45°. In particular, the wedge angle may have a value of about 25° to about 35°. Such wedge angles can be made with a conical milling cutter in a simple and secure manner. An interengagement of corresponding toothings can thus be ensured in a simple manner.

The production of the toothing can be simplified, in particular, by it being formed mirror symmetrical to a toothing mirror plane extending in the longitudinal direction.

In accordance with a further preferred embodiment of the invention, provision may be made that the toothing is configured in such a way that each second surface region defines a second surface region plane, that the second surface region planes of adjacent teeth define a common surface region intersection line, and that the surface region intersection line together with the longitudinal direction encloses an angle of inclination opened in the distal direction. Such a toothing can be formed in a simple manner by a conical milling cutter, the longitudinal axis of which is aligned perpendicularly to the surface region intersection line and is moved in parallel thereto.

It is favorable if the angle of inclination is predetermined by an orientation of the longitudinal axis of the second conical milling cutter during milling relative to the top side and if the longitudinal axis is aligned perpendicularly to the surface region intersection line and together with the longitudinal axis defines a plane extending perpendicularly to the top side. The second conical milling cutter can then be moved in parallel to the surface region intersection line in order to form the second surface regions of adjacent teeth in one single working step. In particular, the angle of inclination may have a value in a range of about 30° to about 50°. For example, it may be about 40°. Furthermore, in particular, an optimal interengagement of corresponding toothings that are formed on two cooperating instruments arms can thus be achieved.

The teeth are favorably configured in such a way that each tooth flank has a notch in the second surface region and that the notch is delimited by the first surface region on the one hand and by the top side on the other hand. This notch, also referred to as a set-back portion, on each tooth flank makes it possible, in particular, for correspondingly formed toothings to be able to interengage into one another so far that top sides of the instrument arms on which the teeth are formed can be brought directly into abutment with one another.

In order to be able to achieve an atraumatic instrument end, it is advantageous if an end face of the toothing facing in the distal direction is rounded.

The end face is preferably configured in such a way that it extends from a bottom side of the instrument arm, which points in a direction opposite to the top side, up to the tooth tip. Thus, in particular, the distal end of the instrument can be completely rounded off, even when two mutually corresponding toothings interengage with one another.

It is advantageous if the end face is configured in such a way that it defines a cylindrical surface and that a cylinder longitudinal axis of the cylindrical surface extends transversely, in particular perpendicularly, to the longitudinal direction and in parallel to the top side. In particular, the cylinder longitudinal axis lies in a plane defined by the top side. Thus, in particular, a semi-cylindrical distal end of the instrument can be achieved when two corresponding toothings are formed on two cooperating instrument arms.

Furthermore, it may be favorable if the end face is configured in such a way that it defines a section of a spherical surface or is of substantially spherical configuration. End faces of the instrument arms formed in that way can contribute, in particular, to a risk of tissue damage with the distal ends of the instrument arms being reduced.

It is favorable if the teeth are configured in such a way that a distance of the tooth tip from the top side is smaller than a thickness of the instrument arm in the region of its distal end and that the thickness is defined by a distance of the top side from the bottom side. A stability required for a use of the instrument can be ensured in this way.

In accordance with a further preferred embodiment of the invention, provision may be made that the instrument is configured having two instrument arms such that formed on a first instrument arm of the two instrument arms is a first toothing, which points in the direction toward a second instrument arm of the two instrument arms, that formed on the second instrument arm is a second toothing, which points in the direction toward the first instrument arm, and that in a closing position of the instrument in which distal ends of the two instrument arms are maximally proximate to one another, the first toothing and the second toothing interengage in one another. It is thus possible, in particular, to form tweezers with corresponding toothings on their distal working arm ends in a simple and fast manner.

gage in one another. It is thus possible, in particular, to form tweezers with corresponding toothings on their distal working arm ends in a simple and fast manner.

In particular, in order to be able to form a symmetrical instrument, it is favorable if the second toothing is configured having one more tooth than the first toothing. For example, one toothing may have three teeth, the other toothing four teeth. In the closing position, the three teeth of the one toothing can then engage into the three respective gaps in the toothing comprising four teeth.

The instrument can be formed in a simple manner if the teeth of the first toothing and the second toothing are identically or substantially identically shaped.

The instrument is preferably configured in the form of tweezers. Using such tweezers, body tissue of humans or animals can be prepared and handled in a simple and secure manner.

Figure 1:
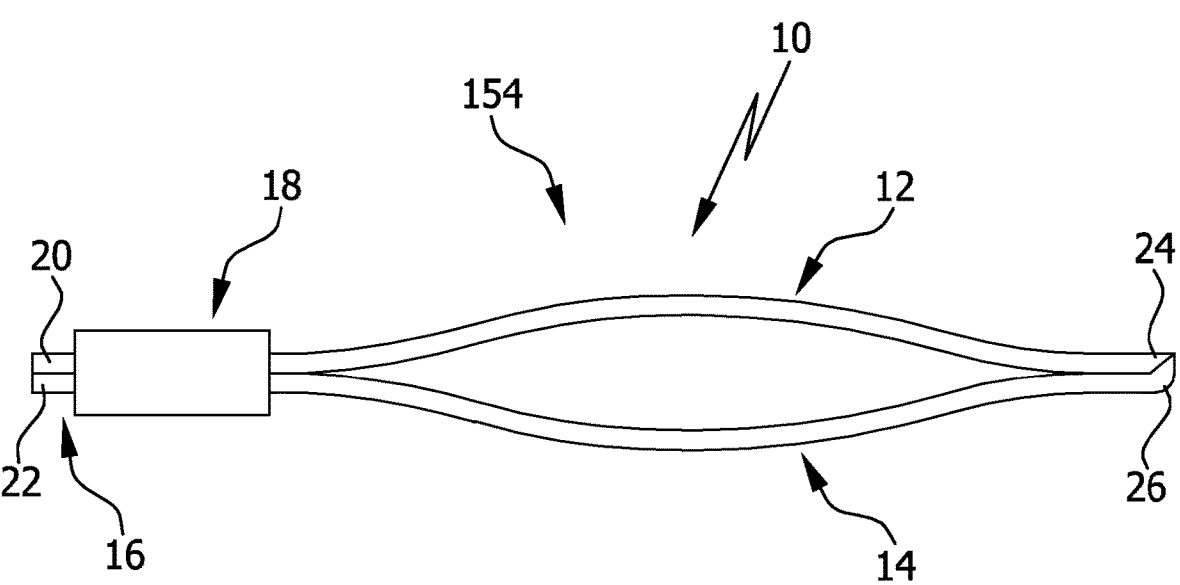
FIG. 1 shows a schematic side view of an embodiment of a medical instrument.

An embodiment of a medical instrument is schematically depicted in FIG. 1 in a closing position. The instrument 10 comprises a first instrument arm 12 and a second instrument arm 14.

The instrument arms 12 and 14 are connected to one another in a proximal end region 16 by means of a sleeve-shaped connecting element 18. The connecting element 18 engages around proximal end portions 20 and 22 of the two instrument arms 12 and 14.

The instrument arms 12 and 14 extend from the connecting element 18 up to distal ends 24 and 26, respectively.

The distal ends 24 and 26 are schematically depicted in FIG. 1 in a maximally proximate position. The instrument 10 adopts this closing position when the instrument arms 12 and 14 are moved toward one another until the distal ends 24 and 26 abut against one another.

Figures 14, 15:
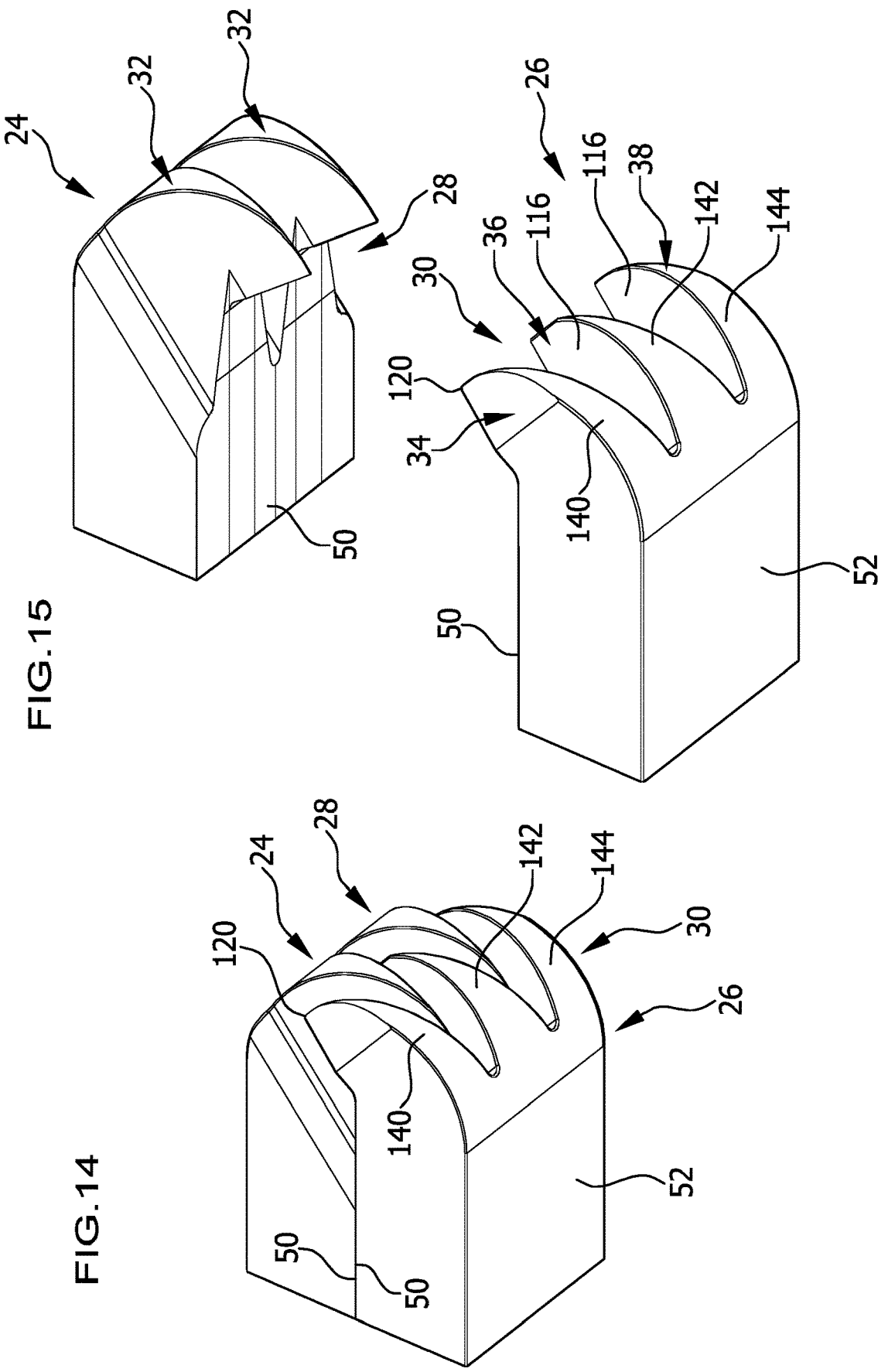
FIG. 14 shows a schematic perspective view of a distal end region of the instrument from FIG. 1 in a closing position.
FIG. 15 shows a schematic perspective view of the distal end region of the instrument from FIG. 1 in an opened position.

The distal ends 24 and 26 are schematically depicted in FIGS. 14 and 15. A first toothing 28 is formed on the distal end 24, a second toothing 30 on the distal end 26. In FIG. 15, the distal ends 24 and 26 are depicted in a mutually separated or opened position. FIG. 14 shows the distal ends 24 and 26 of the instrument 10 in a maximally proximate position, also referred to as a closing position, in which the toothings 28 and 30 interengage in one another.

The first toothing 28 comprises two identically formed teeth 32.

The second toothing 30 comprises teeth 34, 36, and 38. The tooth 36 is configured identically to the teeth 32. The teeth 34 and 38 are configured mirror-symmetrically relative to a toothing mirror plane 40. The toothing mirror plane 40 also defines a tooth mirror plane 42, relative to which the tooth 36 that is arranged between the teeth 34 and 38 is formed.

In the closing position the teeth 32 each engage into a recess between the teeth 34 and 36 on the one hand and between the teeth 36 and 38 on the other hand.

The two toothings 28 and 30 are completely machine made in the case of the embodiment of the instrument 10 depicted in FIG. 1.

In the following, as an example, the formation of the second toothing 30 is discussed in connection with FIGS. 2 to 13.

For forming the second instrument arm 14, in a first step, an instrument arm blank 44 is provided, which defines a distal end region 46 that defines a longitudinal direction 48. A cross section of the instrument arm blank 44 is substantially rectangular and defines a top side 50 and a bottom side 52. The top side 50 and the bottom side 52 extend substantially in parallel to one another and face in opposite directions.

The instrument arm blank 44 is made of a metallic material and is brought into the desired shape by cold forming.

Configured projecting from the top side 50 is a tooth projection 54, which projects from the top side 50 transversely to the longitudinal direction 48. An end face 56 of the instrument arm blank 44 extends perpendicularly to the longitudinal direction 48 and has a height 58 that is about twice as great as a distance 60 between the top side 50 and the bottom side 52. The distance 60 therefore defines a thickness 62 of the instrument arm blank 44.

The tooth projection 54 has a tooth projection top side 64 extending in parallel to the top side. From said tooth projection top side 64, an inclined tooth face 66 extends in the proximal direction up to the top side 50.

In a first machining step, the tooth projection 54 is machined with a cylindrical milling cutter 68. A longitudinal axis 70 of the cylindrical milling cutter 68, about which the cylindrical milling cutter 68 rotates for machining the tooth projection 54, extends perpendicularly to the top side 50.

Two identical grooves 72 are formed on the tooth projection 54 using the cylindrical milling cutter 68, namely by the cylindrical milling cutter 68 being moved in the described orientation in the direction of the arrow 74 in parallel to the longitudinal direction 48. An end face 76 of the cylindrical milling cutter 68 facing in the direction toward the top side 50 contacts the top side 50, but without machining it.

Figure 3:
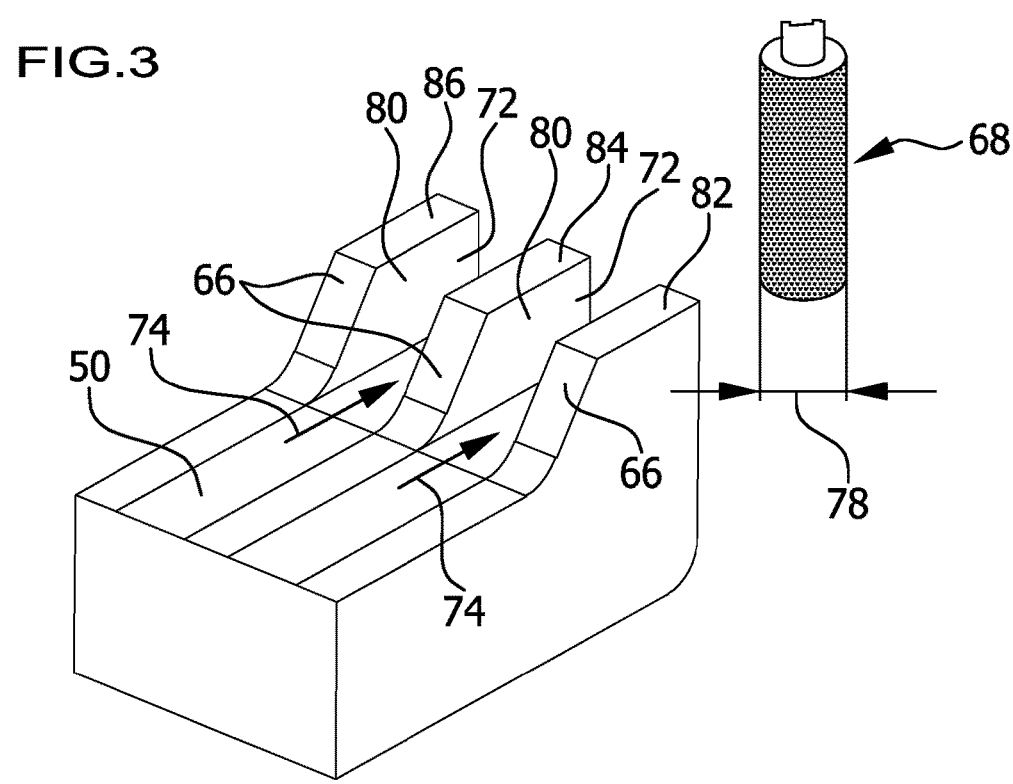
FIG. 3 shows a view similar to FIG. 2 after the first machining step.

The result of this first machining step with two milling operations for forming the grooves 72 is schematically depicted in FIG. 3.

The cylindrical milling cutter 68 has a diameter 78.

The grooves 72 are laterally delimited by surface regions 80 that extend in parallel to one another and face toward one another, as well as by the top side 50 extended between the three remaining projections 82, 84, and 86.

Figure 4:
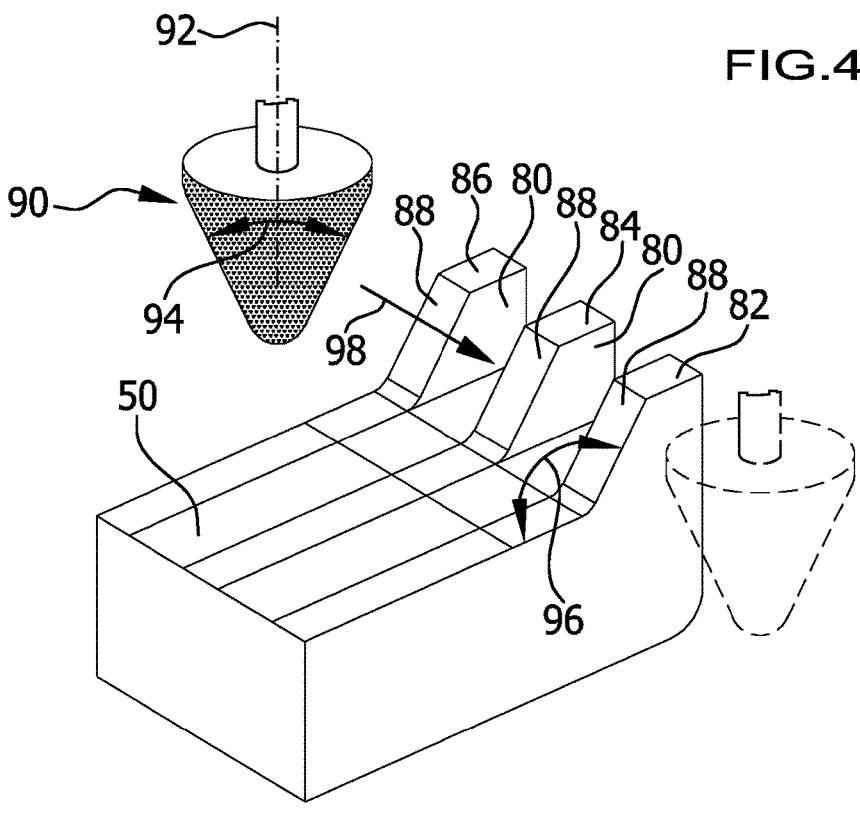
FIG. 4 shows a schematic perspective view of the distal end region of the instrument arm blank prior to performing a second machining step.

An optional machining step of the manufacturing process is schematically depicted in FIG. 4.

In order to form the tooth face 66 in a defined manner, which cannot be reliably achieved with correspondingly high reproducibility by cold forming on the instrument arm blank 44, third surface regions 88 are formed on the projections 82, 84, and 86 by means of a second conical milling cutter. For this purpose, the second conical milling cutter 90 is oriented with its longitudinal axis 92 perpendicular to the top side 50 and is moved along the tooth face 66.

The second conical milling cutter 90 has a cone angle 94. In the embodiment depicted in the Figures, said cone angle 94 is about 70°. An opening angle 96 that is defined between the third surface regions 88 and the top side 50 is about 125°. This corresponds to an angular sum of half the cone angle 94 plus 90°.

The second conical milling cutter 90 is moved in a direction symbolized by the arrow 98 in parallel to the top side 50 in order to form the third surface regions 88.

The machining step depicted in connection with FIG. 4 is optional, as already mentioned. If the tooth face 66 fulfills the given specifications, the described machining of the projections 82, 84, and 86 with the second conical milling cutter 90 can also be forgone.

This optional machining step with the second conical milling cutter 90 may alternatively be performed before the machining step with the cylindrical milling cutter 68.

Figure 5:
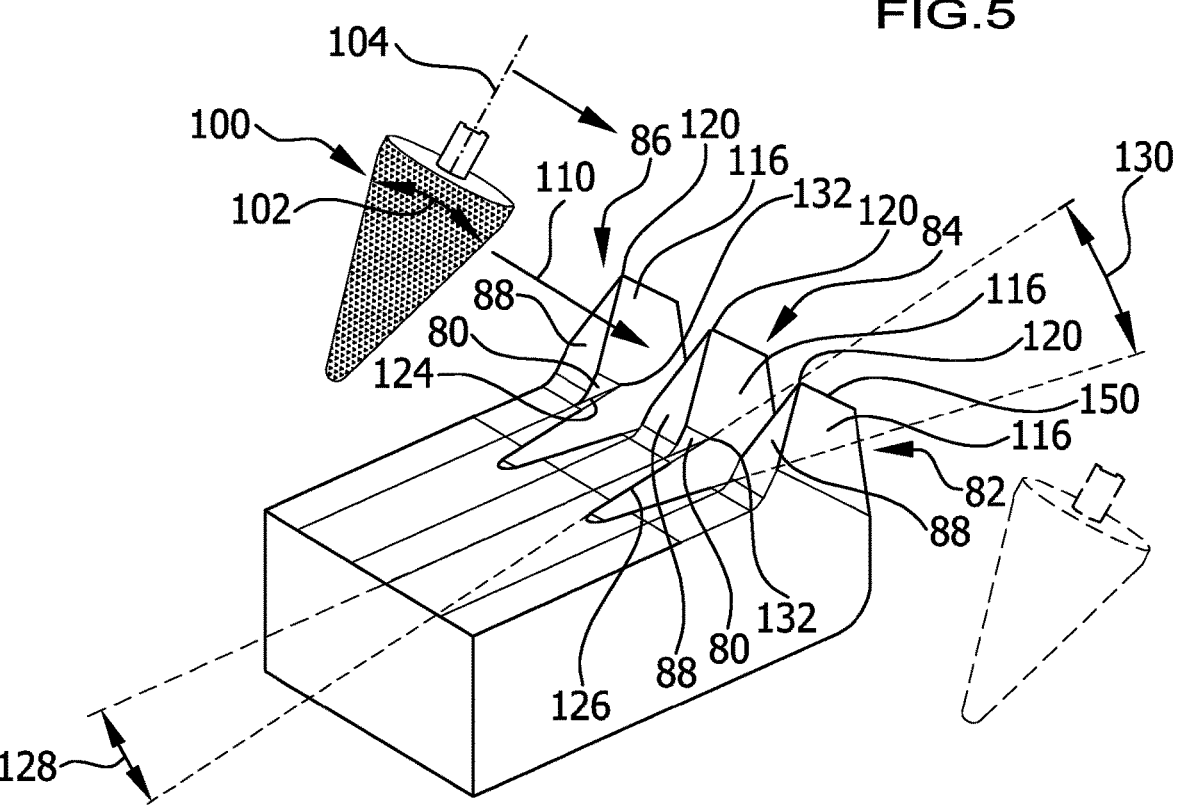
FIG. 5 shows a schematic perspective view of the distal end region of the instrument arm blank after performing a third machining step.
Figures 6, 7, 8:
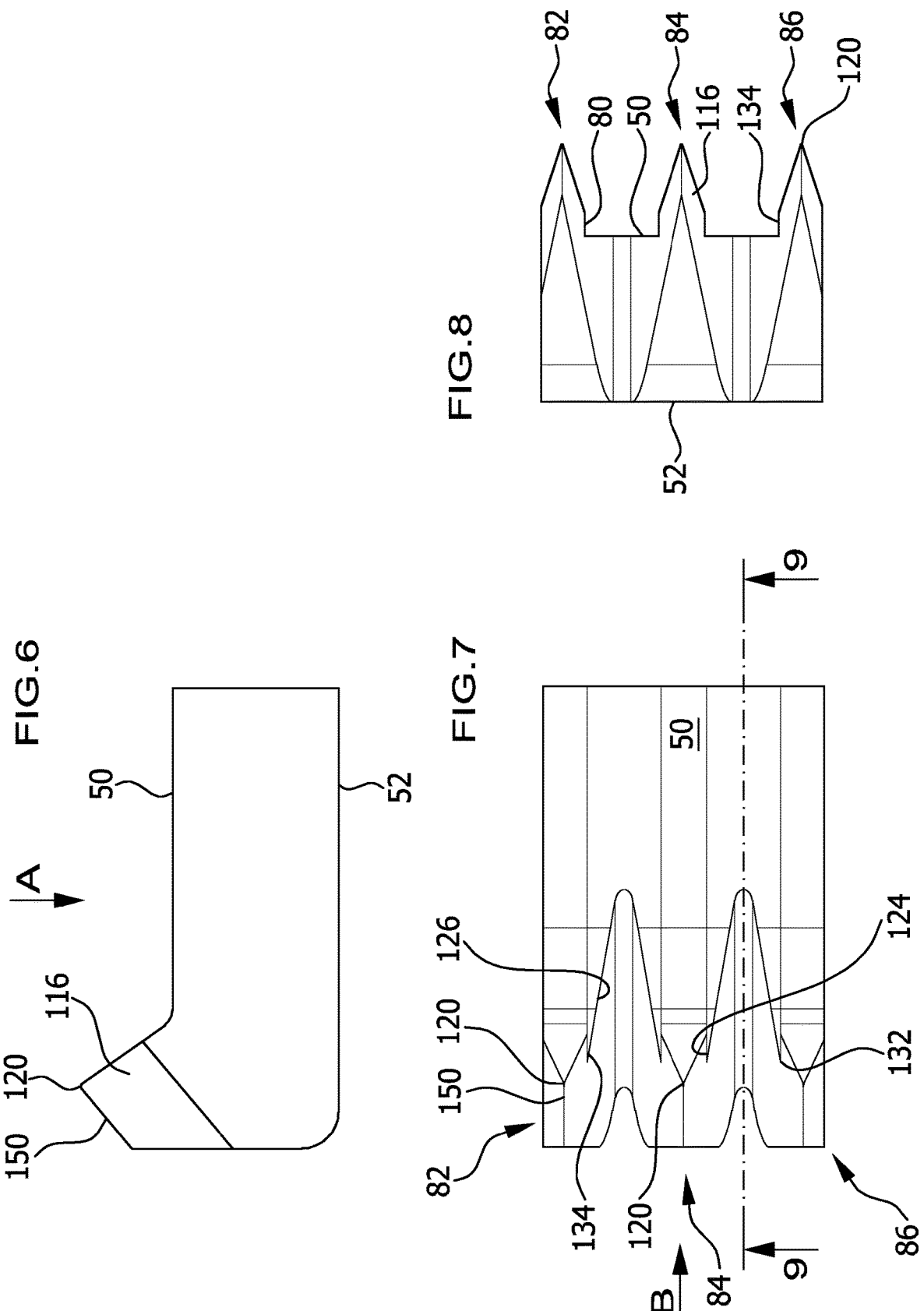
FIG. 6 shows a side view of the machined distal end region of the instrument arm blank from FIG. 5.
FIG. 7 shows a view of the arrangement from FIG. 5 in the direction of the arrow A.
FIG. 8 shows a view of the arrangement from FIG. 7 in the direction of the arrow B.
Figure 9:
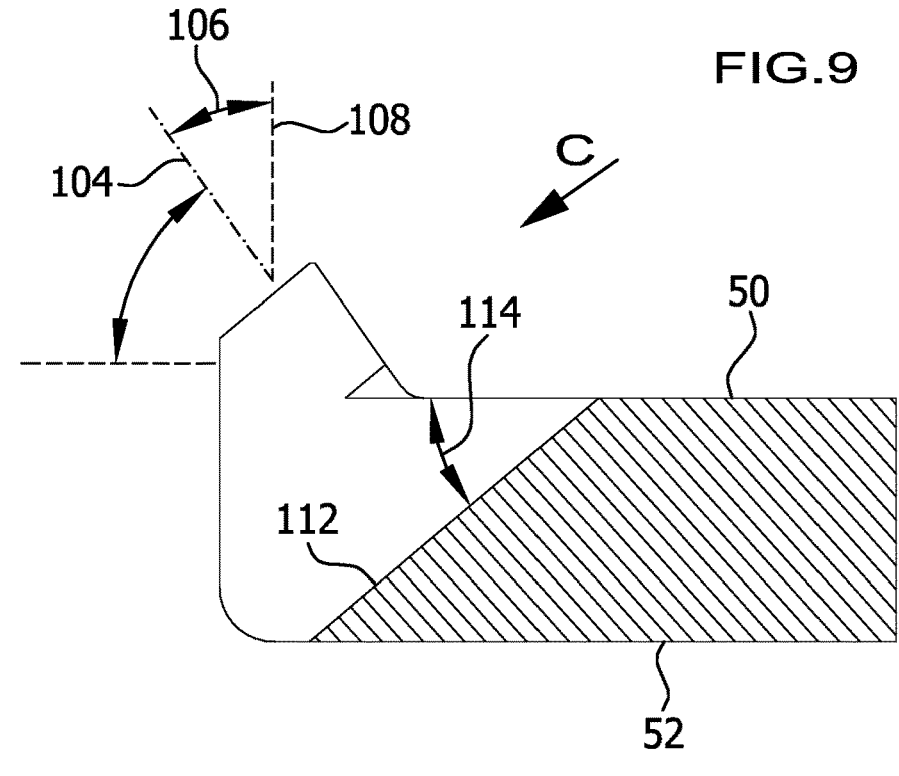
FIG. 9 shows a section view along line 9-9 in FIG. 7.

A third machining step for forming the second toothing 30 is schematically depicted in FIG. 5. In this machining step a first conical milling cutter 100 is used, which defines a cone angle 102. In the embodiment depicted in the Figures, said cone angle 102 is about 30°.

The first conical milling cutter 100 defines a longitudinal axis 104 about which the first conical milling cutter 100 is rotated for machining the distal end region 46.

During milling, the longitudinal axis 104 is inclined relative to the top side 50 by a first milling angle 106. The milling angle 106 between the longitudinal axis 104 and a surface normal 108 of the top side 50 is 40° in the embodiment depicted in the Figures.

The first conical milling cutter 100 is moved obliquely forward in the distal direction in a milling direction symbolized by the arrow 110, such that a wedge-shaped groove is formed between the projections 82 and 84 on the one hand and 84 and 86 on the other hand. A groove base 112 runs in parallel to the milling direction, i.e. in the direction of the arrow 110, and is inclined relative to the top side 50 by an angle of inclination 114, which correspond to the milling angle 106, therefore about 40° in the embodiment depicted in the Figures.

Using the first conical milling cutter second surface regions 116 facing toward one another are formed on the projections 82, 84, and 86. Second surface regions 116 facing toward one another define between them a wedge angle 118, which correspond to the cone angle 102.

The teeth 34, 36, and 38 now almost have their final form. Tooth tips 120 form intersection points of the two second surface regions 116 and of the third surface region 88 of the machined projections 82, 84, and 86.

The projections 82, 84, and 86 define tooth flanks 122 facing toward one another, which are formed primarily by a second surface region 116 and a remainder of a first surface region 80.

Each first surface region 80 defines with the top side 50 a first top side intersection line 124.

Each second surface region 116 defines with the top side 50 a second top side intersection line 126.

First top side intersection lines 124 and second top side intersection lines 126 on the same projection 82, 84 and 86 enclose an acute angle 128 opening in the proximal direction.

The second top side intersection lines 126 of adjacent projections 82, 84, and 86 define between them an acute angle 130 opened pointing in the distal direction.

Furthermore, on each tooth flank 122, a point of intersection 132 is defined between the first top side intersection line 124 and the second top side intersection line 126, wherein the first surface region 80, the second surface region 116, and the top side 50 come into contact at the point of intersection 132.

In addition, each tooth flank 122 comprises a notch 134 in the second surface region 116. The notch 134 is delimited by the first surface region 80 on the one hand and by the top side 50 on the other hand.

In a final machining step, the projections 82, 84, and 86 are rounded off. For this purpose, the remaining regions of the end face 56 are milled or ground off such that an envelope 136 is defined, which forms a section of a cylindrical surface 138. End faces 140, 142, and 144 of the teeth 34, 36, and 38 are thus formed, which face in the distal direction and extend from the bottom side 52 up to the tooth tip 120.

The cylindrical surface 136 is configured concentrically to a cylinder longitudinal axis 146 that extends in parallel to the top side 50 and forms part thereof.

A distance 148 of the tooth tip from the top side 50 is smaller than the thickness 62.

As described, the second toothing 30 comprises three teeth 34, 36, and 38. The first toothing 28 comprises two teeth 32. These are configured in an analogous manner to the tooth 36. The shape of an interspace between the teeth 32 corresponds to a shape of the interspaces between the teeth 34 and 36 as well as 36 and 38.

The particular design of the toothings 28 and 30 makes it possible for the teeth 32 to engage completely into the interspaces between the teeth 34 and 36 as well as 36 and 38, namely so far that the top sides 50 of the two instrument arms 12 and 14 completely abut against one another in the closing position. This property is made possible, in particular, by the configuration of the notches 134 on the tooth flanks 122.

Figure 2:
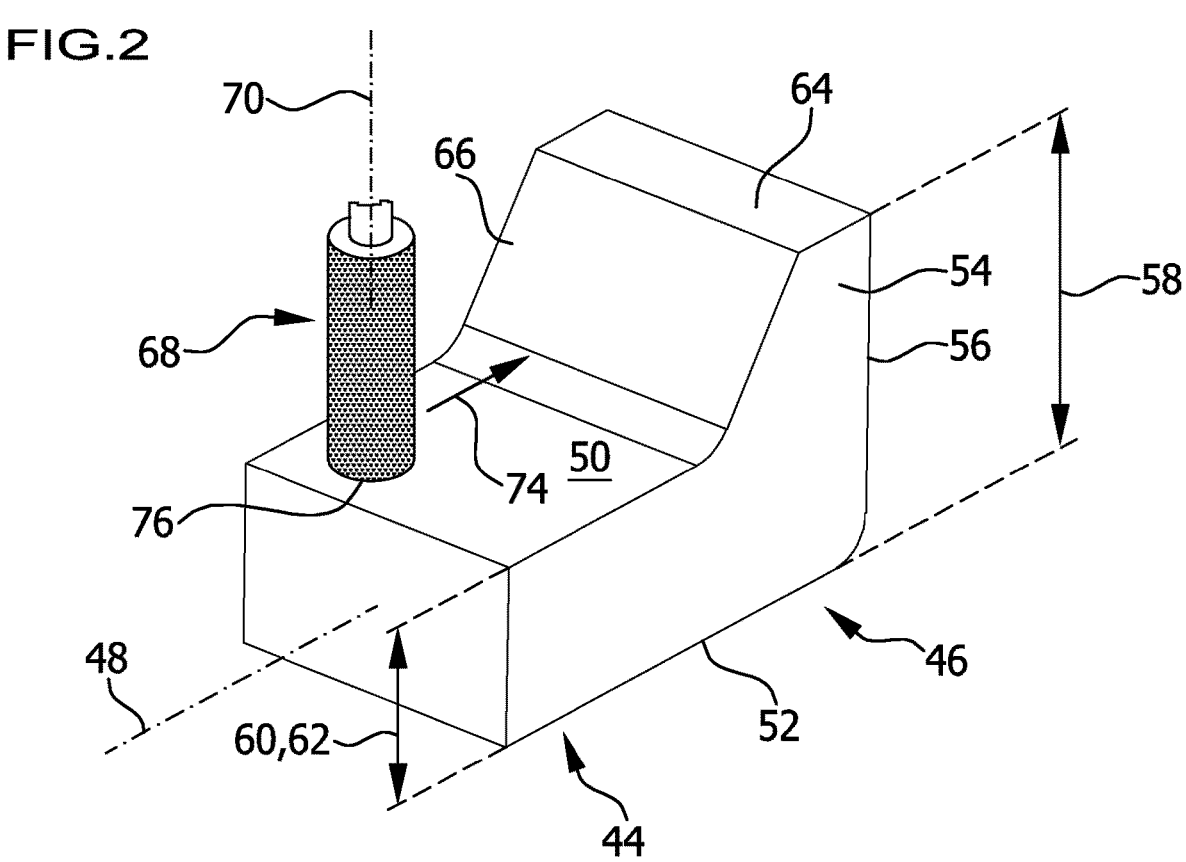
FIG. 2 shows a schematic perspective view of a distal end region of an instrument arm blank prior to a first machining step.

The machining steps depicted in conjunction with FIGS. 2, 3, 5 and their outcome in FIGS. 14 and 15 may be carried out completely by machine. Likewise, the optional machining step described in connection with FIG. 4 may also be carried out completely by machine.

In particular, a CNC machine can be used for machining, which can drive and move the milling tools, namely the cylindrical milling cutter 68, the conical milling cutters 90 and 100, as well as a milling tool, which is not shown in the Figures, for rounding off the teeth 32, 34, 36 and 38 to form the end faces 140, 142 and 144.

Schematically depicted in FIGS. 16 to 21 is a further embodiment of a medical instrument 10. This has a great similarity to the embodiment described in conjunction with FIGS. 1 to 15, such that identical reference numerals were used to denote identical or similar parts and components, in part with a prime symbol.

As an example, FIGS. 16 to 19 show how one of the two instrument arms 12 and 14 of the instrument 10 is formed from an instrument arm blank 44.

Figure 16:
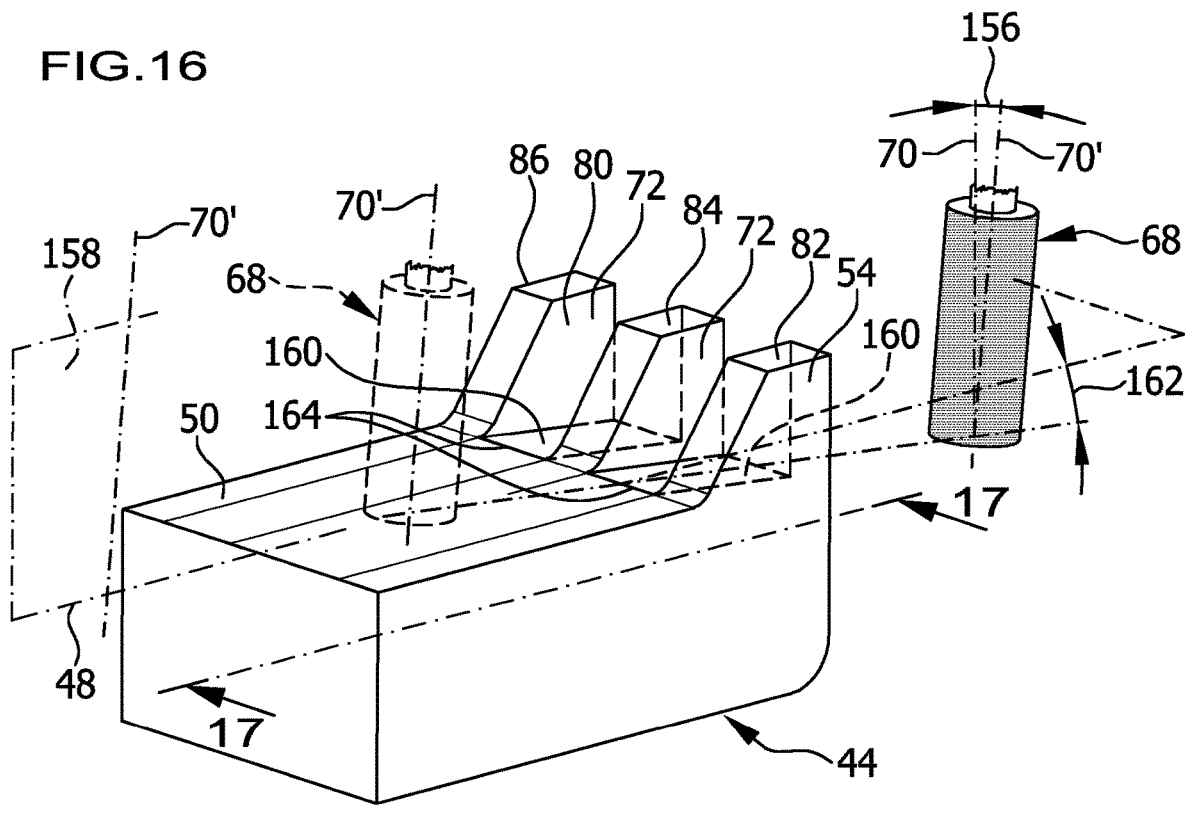
FIG. 16 shows a schematic perspective view of a further embodiment of a distal end region of an instrument arm blank with three teeth during or after a first machining step.

The instrument arm blank 44, which is shown schematically in FIG. 16, has already been machined in a first machining step with the second conical milling cutter 90, as has been explained in more detail above as an example in conjunction with FIG. 4.

In a subsequent machining step, the tooth projection 54 is machined with a cylindrical milling cutter 68. In contrast to the embodiment depicted and described above in FIGS. 2 and 3, the longitudinal axis 70' of the cylindrical milling cutter 80 is inclined by a milling cutter longitudinal axis angle 156 relative to the milling cutter longitudinal axis 70, which defines a surface normal to the top side 50. When milling in the longitudinal direction 48, the longitudinal axis 70' of the cylindrical milling cutter 68 defines a milling plane 158, which runs perpendicular to the top side 50. Furthermore, the longitudinal axis 70' is inclined in the distal direction by the milling cutter longitudinal axis angle 156.

In the manner described, two identical grooves 72 are formed with the cylindrical milling cutter 68 on the tooth projection 54 of the instrument arm blank 44. An end face 76 of the cylindrical milling cutter 68 that faces in the direction toward the top side 50 thus forms a sloped face 160, which is inclined relative to the top side 50 by a slope angle 162.

The sloped face 160 and the top side 50 intersect in a sloped face top side intersection line, which extends transversely, namely perpendicularly, to the longitudinal direction 48.

Figure 17:
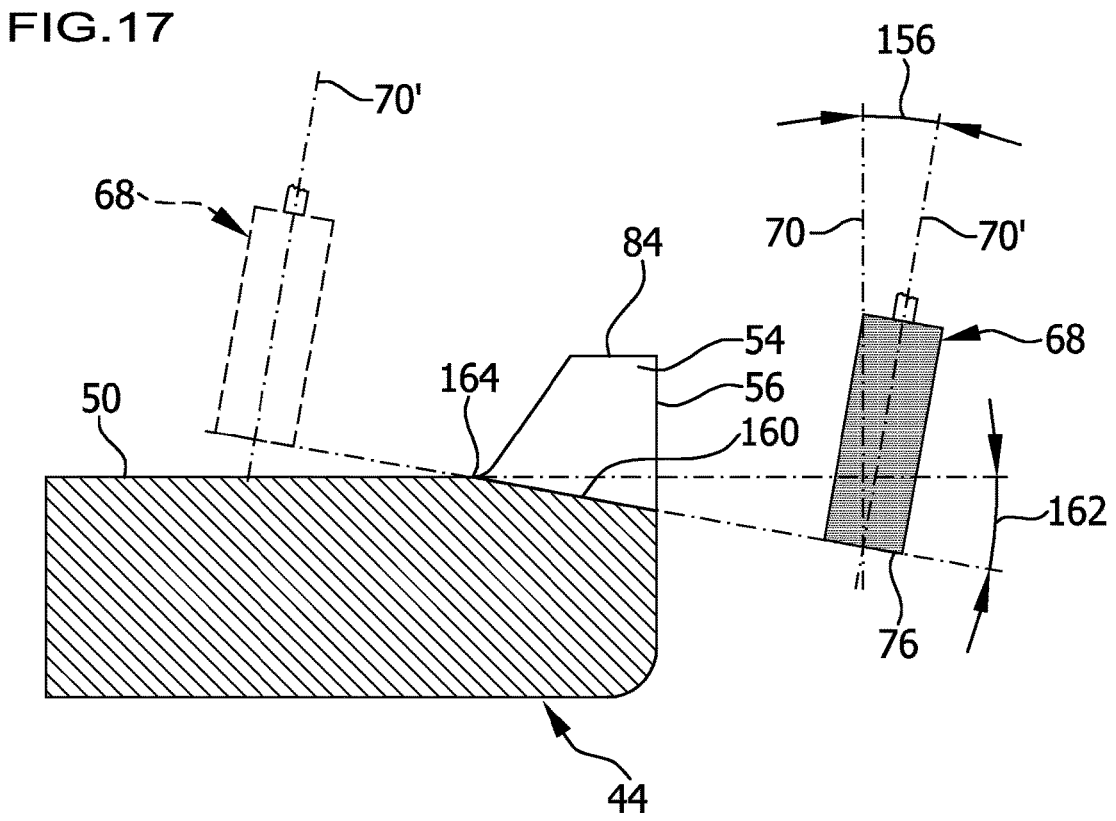
FIG. 17 shows a section view along line 17-17 in FIG. 16.

The described machining of the tooth projection 54 with the cylindrical milling cutter 68 is schematically depicted in FIGS. 16 and 17.

In a further machining step, which is selectively performed before or after machining with the cylindrical milling cutter 68, for forming the second toothing 30, the first conical milling cutter 100 is moved, namely in the manner described above in conjunction with FIG. 5, forward in the distal direction in a milling direction symbolized by the arrow 110, such that a wedge-shaped groove between the projections 82 and 84 on the one hand and 84 and 86 on the other hand is formed. A groove base 112 runs in parallel to the milling direction, i.e. in the direction of the arrow 110, and is inclined relative to the top side 50 by an angle of inclination 114, which corresponds to the milling angle 106, therefore about 40° in the embodiment depicted in the FIGS. 18 to 21.

With the first conical milling cutter 100, in this embodiment, too, second surface regions 116 that face toward one another are formed on the projections 82, 84 and 86, said second surface regions 116 defining between them a wedge angle 118, which corresponds to the cone angle 102.

The slope angle 162 is in a range of about 3° to about 30°. In the embodiment depicted in FIGS. 17 to 21, the slope angle is about 10°.

In this embodiment, too, the projections 82, 84, and 86 define tooth flanks 122 that face toward one another, which are formed primarily by a second surface region 116 and a remainder of a first surface region 80.

The first surface region 80 and the sloped face 160 define a first sloped face intersection line 124'. Furthermore, the second surface region 116 defines with the sloped face 160 a second sloped face intersection line 126'.

The first sloped face intersection line 124' and the second sloped face intersection line 126' of the same tooth flank 120 enclose an acute angle 128' opening in the proximal direction.

The second sloped face intersection lines 126' of adjacent teeth of the toothing define an acute angle 130' opened pointing in the distal direction.

Furthermore, on each tooth flank 122, a point of intersection 132' between the first top side intersection line 124' and the second top side intersection line 126' is defined, wherein the first surface region 80, the second surface region 116, and the sloped face 160 come into contact at the point of intersection 132'.

Furthermore, each tooth flank 122 has a notch 134' in the second surface region 116. The notch 134' is delimited by the first surface region 80 on the one hand and by the sloped face 160 on the other hand.

The machining steps with the cylindrical milling cutter 68 and the first conical milling cutter 100 may alternatively also be carried out in reverse order. This also applies correspondingly to the embodiment schematically depicted in FIGS. 2 to 15. The shape of the toothings 28 and 30 formed therein are not changed as a result.

Figure 18:
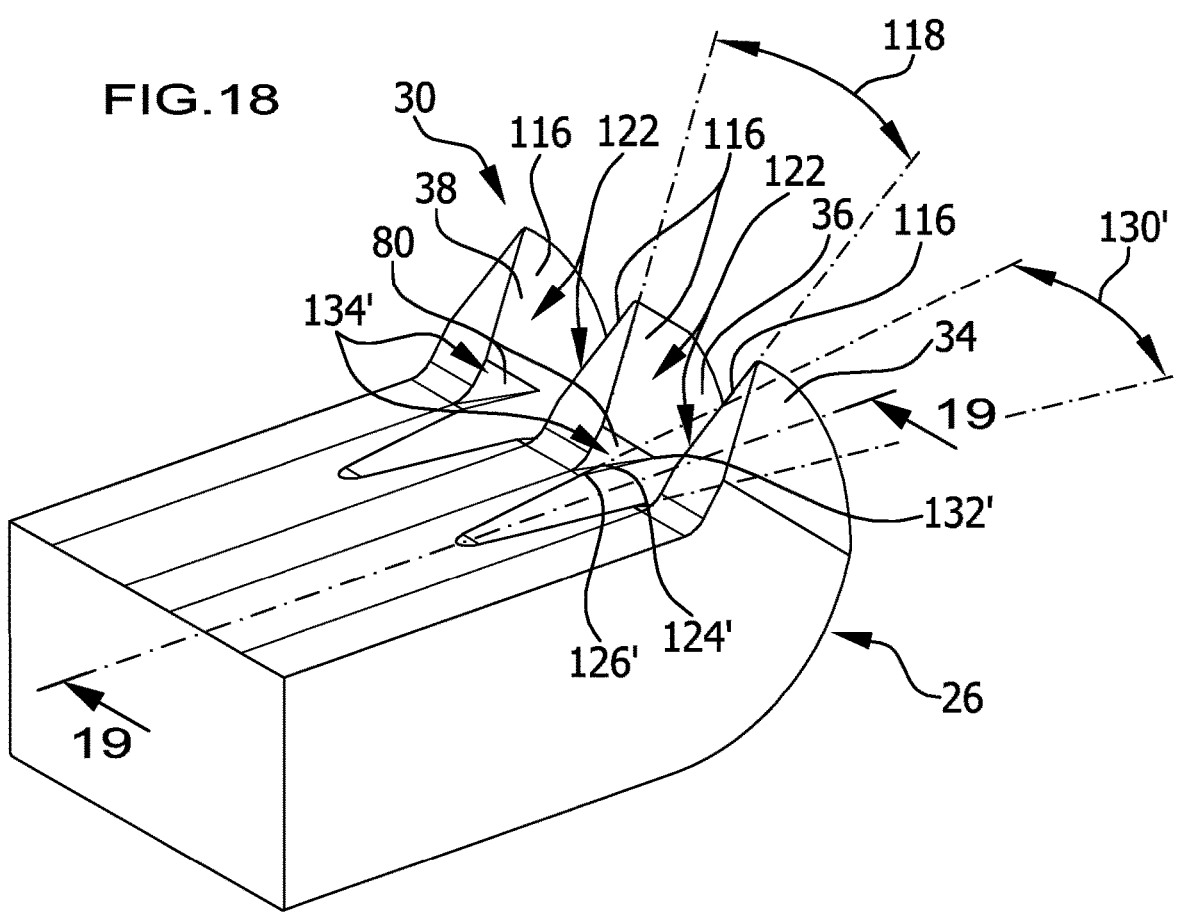
FIG. 18 shows a schematic perspective view of the distal end region of the instrument arm blank from FIGS. 16 and 17 after performing the machining step schematically depicted in FIG. 5 and rounding off the distal end face.
Figure 19:
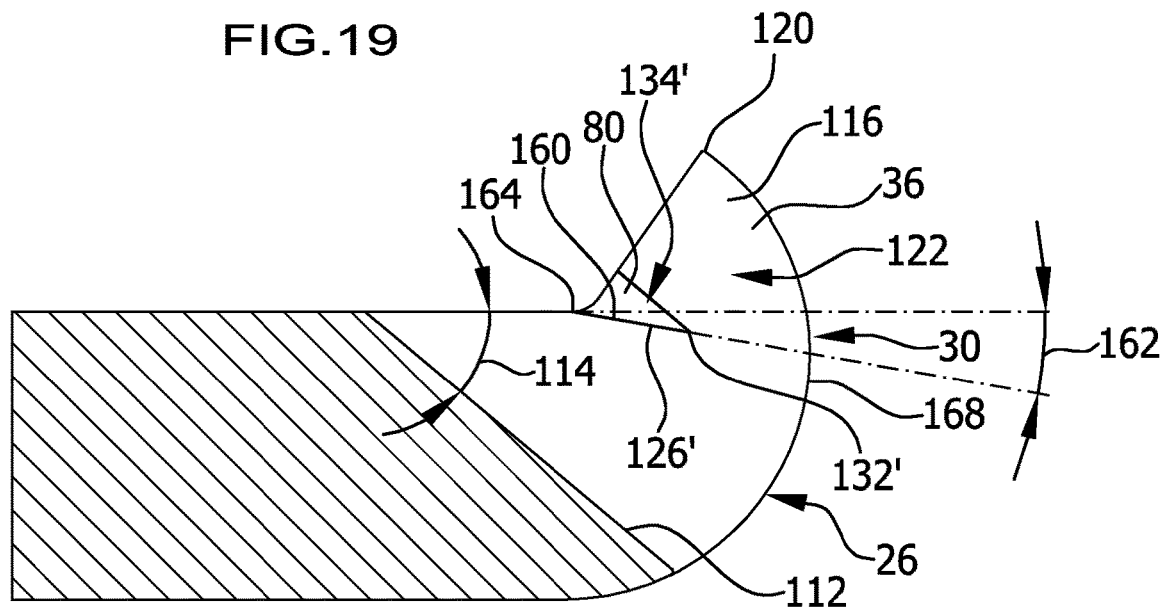
FIG. 19 shows a section view along line 19-19 in FIG. 18.
Figures 20, 21:
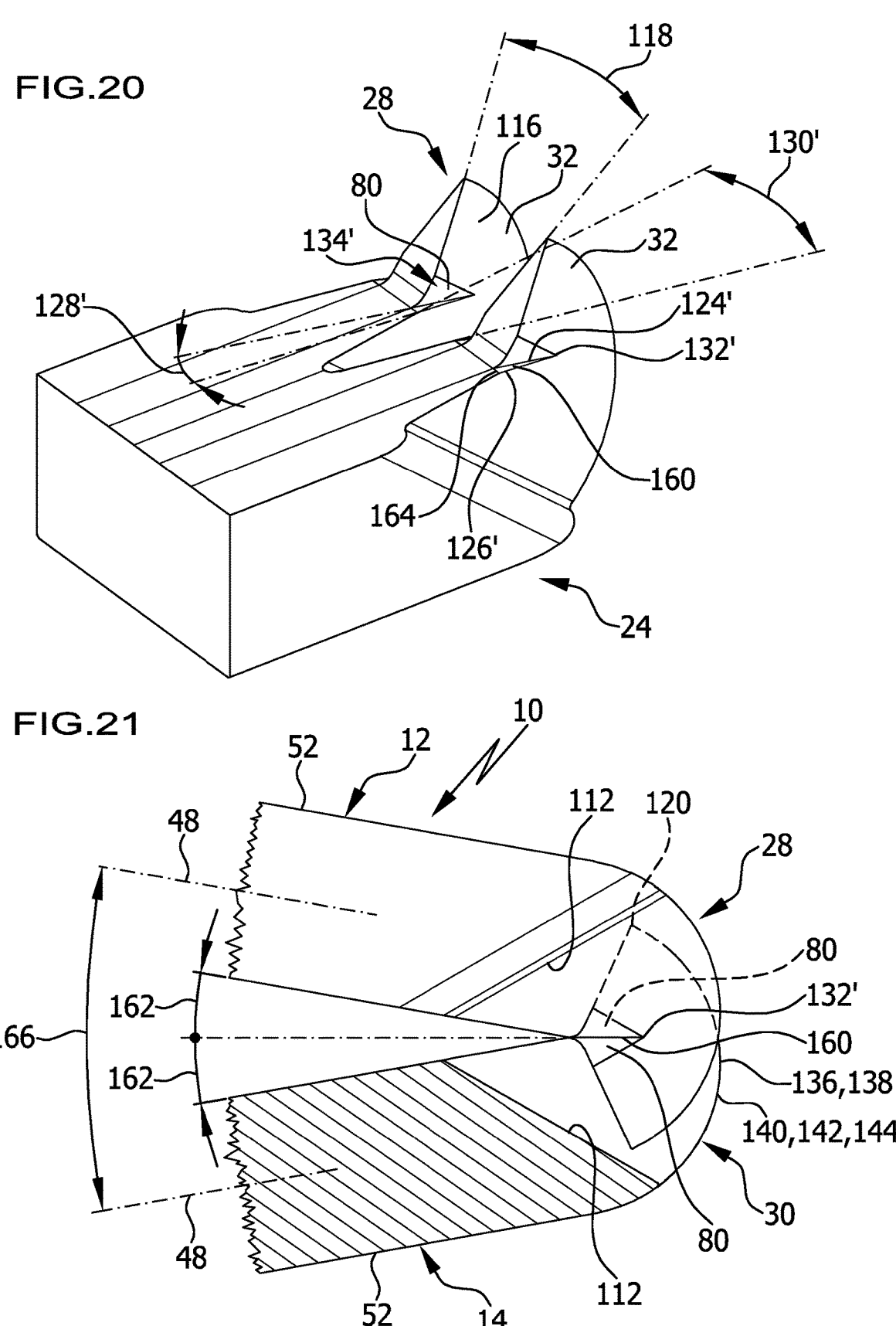
FIG. 20 shows a schematic perspective view of the distal end region of a further embodiment of an instrument body part similar to that in FIG. 18, but with only two teeth.
FIG. 21 shows a partially broken section view similar to FIG. 19 of distal ends of two instrument arms inclined toward one another.

Schematically depicted as an example in FIG. 20 is a distal end 24 of the first instrument arm 12. FIG. 18 schematically shows a distal end 26 of the second instrument arm 14.

The configuration of the sloped faces 160 makes it possible, as schematically shown in FIG. 21, to incline the instrument arms 12 and 14 with their longitudinal directions 48 toward one another, namely by an angle of inclination 166. The sloped faces 160 can then still be brought into surface-to-surface abutment when the angle of inclination 160 corresponds to twice the slope angle 162. The distal ends 24 and 26 of the instrument arms 12 and 14 of the instrument 10 are then configured such that they interengage well and without being caught or jammed if the longitudinal directions 48 of the two instrument arms 12 and 14 enclose an angle of inclination 166 that is not greater than twice the slope angle 162.

The end faces 140, 142 and 144 of the teeth 34, 36 and 38 are rounded or rounded off in the embodiment shown in FIGS. 16 to 21, too. For this purpose, the remaining regions of the original end face 56 of the tooth projection 56 are milled or ground off such that an envelope 136 is defined, which forms a section of a spherical surface 168. End faces 140, 142, and 144 of the teeth 34, 36, and 38 are thus formed, which face in the distal direction and extend from the bottom side 52 up to the tooth tip 120.

The machining steps described in connection with FIGS. 16 to 21 can also be carried out completely by machine, for example with a CNC machine, which can drive and move the milling tools, namely the cylindrical milling cutter 68, the conical milling cutters 90 and 100, and a milling tool, which is not depicted in the Figures, for rounding off the teeth 32, 34, 36 and 38 to form the end faces 140, 142 and 144.

In the manner described, a medical instrument, in particular in the form of tweezers, can be formed in a reproducible manner with constant quality from two instrument arm blanks by machining.

What is claimed is:

1. A method for producing a medical instrument, the method comprising the steps of:

forming at least one instrument arm; and forming a toothing on a distal end of the at least one instrument arm, which at least one instrument arm has a top side that is planar, wherein a distal end region of the at least one instrument arm defines a longitudinal direction, the toothing having at least two teeth that project transversely from the distal end, wherein each of the at least two teeth have tooth flanks facing away from one another, wherein each tooth flank is configured having at least one first surface region that is planar and at least one second surface region that is planar, wherein the at least one first surface region and the at least one second surface region are inclined toward one another by a surface region angle, and wherein the at least one first surface region and the at least one second surface region are formed by milling with a numerically controlled machine, wherein the at least one first surface region is made with a first milling tool having a cylindrical milling cutter, which cylindrical milling cutter is moved in the longitudinal direction, wherein, during milling of the at least one first surface region, a longitudinal axis of the cylindrical milling cutter is oriented both perpendicular to the top side and perpendicular to the longitudinal direction, wherein the at least one second surface region is made with a second milling tool having a first conical milling cutter, which first conical milling cutter is moved obliquely forward in a distal direction in a milling direction which is inclined relative to the top side by an angle of inclination, wherein, during milling of the at least one second surface region, a longitudinal axis of the first conical milling cutter is inclined relative to the top side by an angle of inclination and, together with the longitudinal direction, the longitudinal axis of the first conical milling cutter defines a plane extending perpendicularly to the top side.

2. The method according to claim 1, wherein the toothing projects from the at least one instrument arm in a direction that is transverse with respect to the longitudinal direction.

3. The method according to claim 1, wherein the toothing is configured projecting at least partially beyond the top side.

4. The method according to claim 3, wherein the at least one first surface region defines a first top side intersection line with the top side, and wherein the at least one second surface region defines a second top side intersection line with the top side.

5. The method according to claim 4, wherein:

a) each tooth flank is configured such that the first top side intersection line and the second top side intersection line enclose a first acute angle, b) the toothing is configured such that the second top side intersection lines of adjacent teeth define a second acute angle, c) the toothing is configured in such a way that the at least one first surface region and the at least one second surface region of each tooth flank and the top side come into contact at a point of intersection of the respective first top side intersection line and the respective second top side intersection line, and/or d) the at least two teeth are configured such that each first top side intersection line extends parallel to the longitudinal direction.

6. The method according to claim 3, wherein the at least two teeth are configured such that each tooth flank has a notch in the at least one second surface region and that each notch is delimited by the at least one first surface region and by the top side.

7. The method according to claim 1, wherein each tooth is configured having at least one planar third surface region.

8. The method according to claim 1, wherein the toothing is configured in such a way that each second surface region defines a respective second surface region plane, that the respective second surface region planes of adjacent teeth define a common surface region intersection line for said adjacent teeth, and wherein each common surface region intersection line encloses an angle of inclination with a longitudinal direction of the at least one instrument arm.

* * * * *